United States Patent [19]

Herman et al.

[11] 4,361,712

[45] Nov. 30, 1982

[54] CYANIDE REDUCTION IN NITROAROMATIC PROCESS

[75] Inventors: Frederick L. Herman, Allentown; John E. Sawicki, Breinigsville, both of Pa.

[73] Assignee: Air Products and Chemicals, Inc., Allentown, Pa.

[21] Appl. No.: 151,024

[22] Filed: May 19, 1980

[51] Int. Cl.³ .............................................. C07C 76/02
[52] U.S. Cl. ................................. 568/932; 568/934; 568/935
[58] Field of Search ............... 568/927, 928, 929, 930, 568/931, 932, 933, 934, 935

[56] References Cited

U.S. PATENT DOCUMENTS

| | | | |
|---|---|---|---|
| 1,975,598 | 10/1934 | Davies | 568/932 |
| 2,132,845 | 10/1938 | Castner | 568/932 |
| 2,382,133 | 8/1945 | Stapleton | 568/934 |
| 3,185,738 | 5/1965 | Cossaboon | 568/932 |
| 3,957,889 | 5/1976 | Milligan | 568/932 |
| 3,981,933 | 9/1976 | Cook | 568/932 |
| 4,261,908 | 4/1981 | Schroeder | 568/932 |

*Primary Examiner*—Paul R. Michl
*Attorney, Agent, or Firm*—Russell L. Brewer; E. Eugene Innis

[57] ABSTRACT

The invention relates to a method of eliminating or substantially reducing the amount of cyanide formed in a polynitroaromatic, e.g. dinitrotoluene process. The invention comprises removing the nitrophenolic material from the mononitroaromatic formed in a first stage nitration of toluene prior to feeding the mononitroaromatic to the subsequent nitration zones.

6 Claims, No Drawings

CYANIDE REDUCTION IN NITROAROMATIC PROCESS

Nitroaromatics, particularly dinitrotoluene, are widely used as intermediates in the manufacture of aromatic amines, e.g. toluene diamine which then can be converted to isocyanates for polyurethane manufacture. Commercially, dinitrotoluene, for example, is produced by the mixed acid nitration of toluene, the mixed acid being a mixture of concentrated sulfuric acid and nitric acid. In this process mononitrotoluene is formed in a first nitration stage and then separated from the aqueous phase. The crude mononitrotoluene is then dinitrated with fresh acid in a second nitration stage and the aqeuous phase is recycled to the mononitration stage. The dinitrotoluene then is recovered from the dinitration stage and the impurities removed.

One of the conventional treatments for removing impurities, usually in the form of phenolic materials, e.g. nitrocresols, from dinitrotoluene prior to conversion to toluene diamine production, has been to wash the dinitrotoluene with an aqueous alkaline material, e.g. an alkali metal carbonate or alkali metal hydroxide. These alkaline materials convert the nitrocresols formed during the nitration reaction to water soluble salts which are largely dissolved in the alkaline phase. The remaining salts and alkali are then removed from the dinitrotoluene by washing the dinitrotoluene with water.

It has been observed that during the nitration of aromatics, e.g. polynitroaromatics, a substantial amount of hydrogen cyanide or other cyanide containing compounds are formed. Even though the cyanide compounds are produced in a small amount, as compared to other by-products, the level of production is such that it is in excess of that normally permitted for environmentally acceptable waste streams. Techniques are available for removing the cyanide material from the waste streams, although most of these procedures merely shift the environmental problem from one area to another.

SUMMARY OF THE INVENTION

This invention relates to an improvement in a two step nitration process for producing polynitroaromatics, preferably dinitrotoluene from a mononuclear aromatic compound by the mixed acid technique. The improvement resides in the reduction of cyanide material in the process. Cyanide prevention is achieved by removing nitrophenolic material from the crude mononitroaromatic feed produced in the first nitration stage prior to effecting polynitration of the crude mononitroaromatic in the second and subsequent nitration stages. The level of nitrophenolic material in the crude mononitroaromatic generally should average less than 2000 parts per million by weight in order to achieve cyanide concentrations for environmentally acceptable waste streams.

Several advantages are associated with the process of this invention: A first advantage includes an ability to reduce cyanide formation in the process and provide for environmentally acceptable streams. Secondly, yield loss due to nitrous acid formation via the apparent reaction of nitric acid with nitrophenolic material is reduced.

DESCRIPTION OF THE PREFERRED EMBODIMENTS

It has been found that if the nitrophenolic materials are removed or substantially reduced in the crude mononitroaromatic feed prior to nitrating the mononuclear nitroaromatic in the subsequent nitration zone, the cyanide and nitrous acid concentrations are reduced dramatically. (Nitrophenols are precursors to cyanide in the nitration process, and therefore, extraction of the nitrophenols from the mononitroaromatic prior to subsequent nitration results in a reduction of cyanide generation.)

For purposes herein, the invention is described in a typical dinitrotoluene process with nitrocresols (cresols) being the nitrophenolic material. The removal or reduction of nitrocresols can be accomplished by several techniques all of which are known in the prior art. One of the most common ways is to convert the nitrocresols to water soluble salts. In this regard an alkali metal hydroxide, carbonate or bicarbonate is used to convert the cresols to water soluble salts. The cresols then are effectively removed with the aqueous phase following the first stage nitration. Conventional aqueous alkaline materials suited for practicing the invention include sodium carbonate, ammonium hydroxide, sodium hydroxide, sodium bicarbonate, potassium hydroxide, and other alkaline materials. Solution concentrations for achieving extraction are from about 0.1–50% by weight, and generally 1–10% by weight.

Another technique that can be used for removing the cresols, but is not as common as the alkali metal hydroxide treatment, is the use of any basic ion exchange system. In this system the crude mononitrotoluene is washed with water and is then passed over an ion exchange resin in the basic form. Another modification is that this extraction process can be performed in a cyclic manner, i.e., the water washed mononitrotoluene is passed over the resin to remove cresols, the cresols are then flushed from the resin, and the resin regenerated for subsequent processing of mononitrotoluene. Examples of conventional resinous materials for making the ion exchange resins are urea-formaldehyde resins, and cross-linked copolymers of aromatic divinyl compounds, e.g. a styrene-divinylbenzene copolymer. Generally, the functionality present on the ion exchange resin is an amine group, or a quaternary ammonium group.

Normally, it is important to reduce the cresol content in the crude mononitrotoluene to an average level below about 2000 parts per million by weight, and preferably below about 500 parts per million to provide an environmentally acceptable waste stream. In order to reduce the cresol content to a level such that an environmentally acceptable waste stream, i.e., one that is substantially free of cyanide, is obtained, at least a sufficient quantity of alkaline material must be present to convert the cresols into water soluble salts and preferably the concentration of alkaline material in the wash will be upward of 50 to 500% of the stoichiometric quantity required. Of course if less than stoichiometric quantities of alkaline material are used, reduction in cyanide and nitrous acid formation will be observed, but such reduction will be proportional to the cresol removed and may not be sufficient to meet stringent environmental regulations.

Although not intending to be bound by theory, it is believed the mechanism for cyanide and nitrous acid formation is as follows:

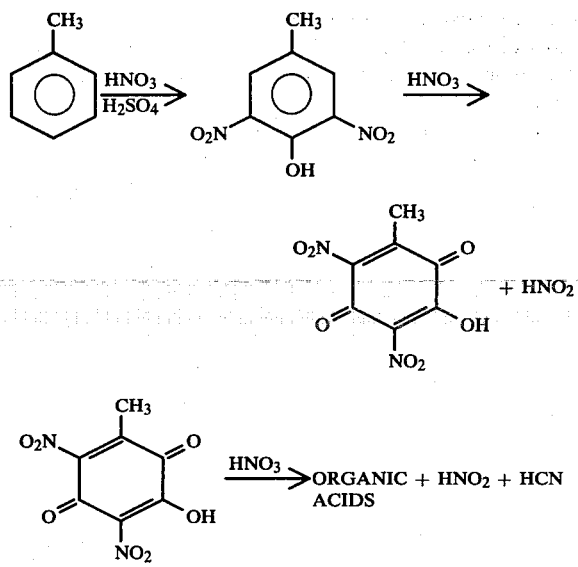

Mononucleararomatics other than toluene which can be used in the practice of this invention include benzene, nitrobenzene, chloronitrobenzene xylene and the like.

The following example is provided to illustrate a preferred embodiment of the invention and is not intended to restrict the scope thereof.

EXAMPLE 1

Toluene was nitrated in conventional manner in a 400 ml. continuous stirred reactor at 50° C. The feed to the first stage nitration reactor consisted of toluene, 43.2% aqueous nitric acid, and 98% sulfuric acid, the feed rate being 10.3 ml per minute for the toluene, 12.5 ml per minute for the nitric acid, and 17.2 ml per minute for the sulfuric acid. The reactor product overflowed into a separator at a rate equal to the feed rate.

The organic phase in the separator averaged about 11% by weight unreacted toluene, 1.2% by weight dinitrotoluene, 87% mononitrotoluene and about 0.3-0.6% nitrocresols. The organic phase then was washed with an equal volume of water and twice with excess alkaline material consisting of an equal weight portion of aqueous 0.1 N sodium hydroxide solution. After washing with the sodium hydroxide solutions, the organic phase was washed again with water to remove all traces of alkali.

The alkali treated crude mononitrotoluene substantially free of nitrocresols was then fed into a 400 ml second step nitration zone at a rate of 12.15 ml per minute along with 8.41 ml per minute aqueous 70% nitric acid and 18.08 ml per minute 98% sulfuric acid. The dinitration zone was maintained at 70° C. Product was continuously removed from the dinitration zone and passed to a separator where it was separated into an organic phase and aqueous phase. The organic phase was washed with an equal volume of water for about 5 minutes and the water analyzed. The concentration of cyanide in the form of HCN in the wash water was 2.7 parts per million by weight. The spent acid contained 895 parts per million by weight nitrous acid.

A control experiment was performed in accordance with the above dinitration procedure except that the crude mononitrotoluene containing the 0.3-0.6% nitrocresols obtained from the first stage nitration was fed to the second stage dinitration without being washed with the aqueous sodium hydroxide solution. The HCN content of the wash water contained in the organic phase fom the dinitrator was 86 parts per million and the spent acid phase contained 2970 parts per million nitrous acid.

These runs show that the reduction or removal of cresols from the crude mononitrotoluene feed to the dinitration zone is effective for reducing both cyanide and nitrous acid concentration in the waste effluent and spent acid from the dinitration zone. Another significant advantage of the processes utilizing the alkali wash of crude mononitrotoluene is that the dinitrotoluene product may have significantly lower quantities of cresols present and may not require alkali treatment. If, however, an alkali wash is utilized for the dinitrotoluene product, particularly where the dinitrotoluene is used for toluene diamine manufacture, the alkali wash solution for washing the dinitrotoluene may be recycled to the crude mononitrotoluene wash cycle to maintain waste water effluent at a low level.

What is claimed is:

1. In a process for producing a polynitroaromatic compound from a mononucleararomatic compound which comprises:

nitrating the mononucleararomatic compound in a first stage nitration zone with an aqueous mixture of sulfuric and nitric acid to form an organic phase containing mononitroaromatic and by-product nitrophenolic material and an aqueous phase containing spent acid;

separating the organic phase from the aqueous phase containing spent acid;

nitrating the mononitroaromatic contained in the organic phase in a second stage nitration zone using an aqueous mixture of sulfuric and nitric acid to form an organic phase containing a polynitroaromatic compound and an aqueous acid phase; and separating the organic phase from the aqueous phase; and recovering the polynitroaromatic compound from the organic phase;

the improvement for reducing cyanide and nitrous acid formation during the process for producing polynitroaromatic compound which comprises:

reducing the by-product nitrophenolic material present in the organic phase from the first stage nitration zone prior to nitrating the mononitroaromatic in the second stage nitration zone.

2. The process of claim 1 wherein said nitrophenolic material is reduced from the mononitroaromatic by washing the organic phase containing mononitroaromatic with an aqueous alkaline medium.

3. The process of claim 2 wherein said aqueous alkaline medium is an aqueous solution of an alkali metal or ammonium hydroxide, carbonate or bicarbonate.

4. The process of claim 3 wherein said aqueous alkaline medium is an aqueous solution of sodium or potassium hydroxide, carbonate or bicarbonate.

5. The process of claim 3 wherein the concentration of the alkaline medium for reducing the nitrophenolic material is from 0.1-50% by weight.

6. The process of claim 5 wherein said mononucleararomatic compound is toluene and said polynitroaromatic compound is dinitrotoluene.

* * * * *